United States Patent
Ciliberto et al.

(10) Patent No.: US 6,565,869 B1
(45) Date of Patent: May 20, 2003

(54) USE OF CNTF (CILIARY NEUROTROPHIC FACTOR) RECEPTOR ACTIVATORS FOR THE TREATMENT OF OBESITY

(75) Inventors: Gennaro Ciliberto, Rome (IT); Patrizia Costa, Rome (IT); Giacomo Paonessa, Rome (IT); Domenico Lazzaro, Rome (IT); Isabelle Gloaguen, Scoppito L'Aquila (IT); Annalise Di Marco, Rieti (IT); Anna De Martis, Rome (IT); Ralph Laufer, Rome (IT); Riccardo Cortese, Rome (IT)

(73) Assignee: Istituto di Ricerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/308,368

(22) PCT Filed: Nov. 18, 1997

(86) PCT No.: PCT/IT97/00283

§ 371 (c)(1),
(2), (4) Date: Jul. 19, 1999

(87) PCT Pub. No.: WO98/22128

PCT Pub. Date: May 28, 1998

(30) Foreign Application Priority Data

Nov. 19, 1996 (IT) .......................................... RM96A0790

(51) Int. Cl.[7] .............................. A61F 2/02; A01N 37/18; A61K 38/18; A61K 38/24; A61K 38/27
(52) U.S. Cl. ............................ 424/423; 514/2; 514/21; 530/350; 530/399
(58) Field of Search ..................... 424/423; 514/2, 514/21; 530/350, 399

(56) References Cited

U.S. PATENT DOCUMENTS

| | | | |
|---|---|---|---|
| 4,997,929 A | 3/1991 | Collins et al. |
| 5,011,914 A | 4/1991 | Collins et al. |
| 5,141,856 A | 8/1992 | Collins et al. |
| 5,166,317 A | 11/1992 | Wallace et al. |
| 5,349,056 A | 9/1994 | Panayotatos |
| 5,426,177 A | 6/1995 | Davis et al. |
| 5,441,937 A | 8/1995 | Lynnworth et al. |

(List continued on next page.)

FOREIGN PATENT DOCUMENTS

| | | |
|---|---|---|
| WO | WO91/04316 | 4/1991 |
| WO | WO93/02206 | 2/1993 |
| WO | WO93/10233 | 5/1993 |
| WO | WO94/09134 | 4/1994 |
| WO | WO 98/01149 | 1/1998 |

OTHER PUBLICATIONS

DiMarco, A. et al., Identification of ciliary neurotrophic factor (CNTF) residues essential for Leukemia inhibitory factor receptor binding and generation of CNTF receptor antagonists, Proc. Natl. Acad Sci. USA, vol. 93, pp. 9247–9252, Aug. 1996.

(List continued on next page.)

Primary Examiner—Carlos Azpuru
(74) Attorney, Agent, or Firm—Sheldon O. Weber; Jack L. Tribble

(57) ABSTRACT

The present invention refers to the use of hCNTF (human ciliary neurotrophic factor), mutants thereof or other molecules that activate the CNTF receptor, for the preparation of drugs for the treatment of obesity and associated disease, for example hyperglycemia. FIG. 1 shows the anti-obesity effect of hCNTF and leptin on body weight (left panels) and on food intake (right panels) in genetically obese mice and in mice with diet-induced obesity (DIO).

22 Claims, 10 Drawing Sheets

U.S. PATENT DOCUMENTS

| | | |
|---|---|---|
| 5,470,952 A | 11/1995 | Stahl et al. |
| 5,593,857 A | 1/1997 | Higaki et al. |
| 5,648,334 A | 7/1997 | Davis et al. |
| 5,691,313 A | 11/1997 | Russell |
| 5,780,600 A | 7/1998 | Collins et al. |
| 5,846,935 A | 12/1998 | Panayotatos |
| 5,849,897 A | 12/1998 | Davis et al. |
| 5,892,003 A | 4/1999 | Davis et al. |
| 5,955,290 A | 9/1999 | Stahl et al. |
| 6,143,714 A | 11/2000 | Wong et al. |

OTHER PUBLICATIONS

Saggio, I. et al., CNTF variants with increased biological potency and receptor selectivity define a functional site of receptor interaction, The EMBO Journal, vol. 14, No. 13, 3045–3054 pps, Jul. 1995.

Fantuzzi, G. et al., Ciliary neurotrophic factor (CNTF) induces serum amyLoid A, hypogLycemia and anorexia, and potentiates IL–1 induced corticosterone and IL–6 production in mice, Cytokine, vol. 7, No. 2, 150–156pps, Feb. 1995.

Sarraf, P. et al., Multiple Cytokines and acute inflammation raise mouse Leptin Levels: potential role in inflammatory anorexia, The Journal of Experimental Medicine, vol. 185, No. 1, 171–175 pps, Jan. 1997.

Gloaguen, I. et al., Ciliary neurotrophic factor corrects obesity and diabetes associated with Leptin deficiency and resistance, Proc. Natl. Acad. Sci. USA, vol. 94, 6456–6461 pps, Jun. 1997.

Poduslo, J. F. et al., Permeability at the blood–brain and blood–nerve barriers of the neurotrophic factors: NGF, CNTF, NT–3, BDNF, Molecular Brain Research, vol. 36, 280–286 pps, Sep. 1996.

ALS CNTF Treatment Study Group, A double–blind placebo–controlled clinical trial of subcutaneous recombinant human ciliary neurotrophic factor (rHCNTF) in amyotrophic lateral sclerosis, Neurology, vol. 46, 1244–1249 pps, May 1996.

Miller, R. G. et al., A Placebo–controlled Trial of Recombinant Human Ciliary Neurotrophic (rhCNTF) Factor in Amyotrophic Lateral Sclerosis, Ann Neurol, vol. 39, 256–260 pps, Feb. 1996.

Halaas, J. L. et al., Weight–Reducing Effects of the Plasma Protein Encoded by the obese Gene, Science, vol. 269, 543–546 pps, Jul. 1995.

Pelleymounter, M. A. et al., Effects of the obese Gene Product on Body Weight Regulation in ob/ob Mice, Science, vol. 269, 540–543 pps, Jul. 1995.

Henderson, J. T. et al., Systemic Administration of ciliary Neurotrophic Factor Induces Cachexia in Rodents, J. Clin. Invest., vol. 93, 2632–2638 pps, Jun. 1994.

Panayotatos, N. et al., Exchange of a Single Amino Acid Interconverts the Specific Activity and Gel Mobility of Human and Rat Ciliary Neurotrophic Factors, The Journal of Biological Chemistry, vol. 268, No. 25, 19000–19003 pps, Sep. 1993.

Di Marco, Annalise et al., "Identification of ciliary neurotrophic factor (CNTF) residues essential for leukemia inhibitory factor receptor binding and generation of CNTF receptor antagonists.", Proc. Natl. Acad. Sci. USA, vol. 93, pp. 9247–9252 (1996).

Saggio, Isabella et al., "CNTF variants with increased biological potency and receptor selectivity define a functional site of receptor interaction.", The Embo Journal, vol. 14, No. 13, pp. 3045–3054 (1995).

Fantuzzi, Giamila et al., "Ciliary neurotrophic factor (CNTF) induces serum amyloid A, hypoglycemia and anorexia, and potentiates IL–1 induced corticosterone and IL–6 production in mice.", Cytokine, vol. 7, No. 2, pp. 150–156 (1995).

Sarraf, Pasha et al., "Multiple cytokines and acute inflammation raise mouse leptin levels: potential role in inflammatory anorexia.", The Journal of Experimental Medicine, vol. 185, No. 1, pp. 171–175 (1997).

Gloaguen, Isabelle et al., "Ciliary neurotrophic factor corrects obesity and diabetes associated with leptin deficiency and resistance.", Proc. Natl. Acad. Sci. USA, vol. 94, pp. 6456–6461 (1997).

USE OF CNTF (CILIARY NEUROTROPHIC FACTOR) RECEPTOR ACTIVATORS FOR THE TREATMENT OF OBESITY

CROSS REFERENCE TO RELATED APPLICATION

The present application is the national stage under 35 U.S.C. 371 of PCT/IT97/00283, filed Nov. 18, 1997.

DESCRIPTION

The subject of the present invention is the use of molecules that activate the CNTF (ciliary neurotrophic factor) receptor—such as hCNTF (human CNTF) or mutants of hCNTF—as active principles in the formulation of pharmaceutical compositions suitable for the treatment of obesity and of related diseases. The term hCNTF mutant is intended to mean an amino acid sequence that can in theory be derived from hCNTF by substitution of one or more amino acids.

Obesity, which affects >30% of the adult population in the industrial world, is a major public health problem, since it is associated with type II diabetes, hypertension, hyperlipidemia and increased mortality rate. Obesity is the result of a positive energy balance, as a consequence of an increased ratio of caloric intake to energy expenditure. Treatment is generally unsuccessful due to the operation of mechanisms that restore adipose mass after both intentional or unintentional changes (1). The lipostasis theory postulates that the size of the body fat depot is regulated by a feedback loop, constituted by adipocyte-derived circulating molecules that act on the hypothalamus to decrease appetite and increase energy expenditure (2).

The recently identified 16-kilodalton plasma protein leptin (3) fulfills many of the criteria expected from such a lipostatic hormone. It is expressed in adipose tissue, and its plasma levels are highly correlated with body mass index in rodents and humans (4). The absence of leptin in obese (ob/ob) mutant mice leads to a massive increase in body fat, which can be reversed by systemic administration of the recombinant protein (5, 6, 7). However, human obesity does not appear to be due to deficient expression of leptin, since leptin mRNA and plasma protein levels were shown to be increased in obese versus lean subjects (4). Thus, obese humans may be insensitive to the lipostatic effect of leptin, possibly due to a defect at the level of leptin transport, leptin receptor activity, or post-receptorial signalling mechanisms (8).

There is thus a need in this specific field for new pharmacological agents capable of correcting obesity in people who are resistant to leptin.

Leptin resistance is a characteristic feature of the diabetic (db/db) mouse mutant, which expresses a truncated form of the leptin receptor lacking most of the intracytoplasmic domain (9). An animal model that more closely resembles human obesity is that of mice rendered obese by feeding a high-fat diet (DIO mice). Similar to human obese subjects, DIO mice have elevated plasma levels of leptin (4), suggesting that they are relatively insensitive to the weight-reducing effects of the hormone.

The present invention provides biologically active anti-obesity agents that can reverse obesity, as well as hyperglycemia and hyperinsulinemia associated therewith.

The subject of the present invention is therefore the use of substances that activate the CNTF receptor for the preparation of drugs for treatment of obesity and related diseases. These substances can be hCNTF (human ciliary neurotrophic factor; SEQ ID NO: 1) itself or mutants thereof (see for instance SEQ ID NOS:2 to 28). Good results have been obtained using the hCNTF mutant (Ser166Asp/Gln167His) hCNTF (10), which, from position 159 to position 178, has the following amino acid sequence (shown as SEQ ID NO: 5 in the annexed sequence listing):

Leu Lys Val Leu Gln Glu Leu Asp His Trp Thr Val Arg Ser Ile His Asp Leu Arg Phe [for sake of simplicity, this hCNTF mutant will be referred to hereinafter also as DH-CNTF]. For sake of simplicity, in the annexed sequence listing, it has been indicated only the portion from position 159 to position 178 of the mutants SEQ ID NOS: 2 to 22.

A further subject of the invention is the use of DNA coding for hCNTF or mutants thereof for the preparation of compositions for the treatment of obesity and diseases related thereto.

The present invention also has as its subject a drug for the treatment of obesity and the reduction of body weight, containing, as at least one of its active principles, hCNTF or a mutant thereof, and comprising a pharmaceutically acceptable vehicle. A pharmaceutically acceptable vehicle is intended to be a vehicle that is not dangerous for the patient, that does not degrade or deactivate the active principles or that does not interfere with the effects thereof. The preferred vehicle is a physiological saline solution, but other pharmaceutically acceptable vehicles can be used, and will easily be identified by those skilled in the art. In an embodiment that has shown good results hCNTF or mutants thereof can be used in combination with leptin: in this case the ratio wild type or mutant CNTF/leptin can be selected in the range 1:500 to 1:5, preferably 1:100 to 1:25.

hCNTF or hCNTF variants can be administered to patients in need of treatment in doses ranging from about 1 to 10,000 µg/kg body weight. A preferred dose is between 10 and 1000 µ/kg body weight. A typical daily dose for an adult is between 1 and 100 mg. The necessary amount of active principle according to the invention can be administered in a single daily dose or in multiple doses throughout the day. The treatment regime can require administration for prolonged periods. The size of the dose administered must be determined by a physician and will depend on a number of factors, such as the nature and gravity of the disease, the age and state of health of the patient and the patient's tolerance to the drug itself.

In a specific embodiment, hCNTF or a mutant thereof can be used for treatment of obese patients by means of a short-term (1–2 weeks) daily administration, in order to obtain a rapid, significant decrease in body weight (5–10%), which can be maintained subsequently using an appropriate diet and/or physical exercise.

The active protein molecules can be formulated for parenteral, nasal, bronchial or transdermal administration. The pharmaceutical composition according to the present invention is preferably administered parenterally by means of an injection. In the preferred embodiment, parenteral administration is subcutaneous or intramuscular. Other effective methods of administration are intravenous injections, slow-release parenteral formulations, inhalant mists, or suppositories. In the slow-release formulation the primary solvent can be either of an aqueous or of a non-aqueous type. Furthermore, the vehicle can contain other pharmacologically acceptable excipients to maintain or modify the pH, viscosity, clarity, colour, sterility, stability, speed of dissolution or odor of the formulation. Similarly, the vehicle can also contain other pharmacologically acceptable excipients to modify or maintain the stability, speed of dissolution, release, or absorption of the active principle. These excipients are substances that are normally used to formulate doses for parenteral administration, both in the form of single doses and in the form of multiple doses.

As mentioned above, the preferred parenteral form of administration of the formulation according to the invention is subcutaneous or intramuscular. The most preferred form of parenteral administration is subcutaneous. To obtain the required daily dose of active principle, it is possible to resort to single or repeated subcutaneous or intramuscular injections. In a preferred embodiment of the invention, the dose of active principle is between 10 and 1000 µg/kg/day. For the treatment of obesity, it may be desirable to administer the active principle periodically. Periodic administration may take the form of monthly, bi-weekly, weekly, daily or hourly administration. The required frequency of administration will be apparent to those treating the patient on the basis of standard observational techniques.

It is also possible to consider oral administration of the pharmaceutical formulations according to the invention. In this case, the active principle administered is preferably encapsulated. The encapsulated active principle can be formulated with or without the vehicles usually employed in the preparation of solid doses. Preferably, the capsule is made in such a way that the active portion of the formulation is released in the gastro-intestinal tract when bioavailability is maximized and pre-systemic degradation is minimized. The formulation can also include further excipients with the aim of facilitating absorption of the active principle. It is also possible to use diluting agents, flavouring, low melting-point waxes, vegetable oils, lubricants, suspending agents, capsule disintegration agents and binding agents.

Independently of the method of administration, the specific dose is calculated according to the approximate body weight of the patient. Further refinement of the calculations necessary to determine the appropriate dose for treatment is routinely made by those of ordinary skill in the art, who are capable of reaching these results without the need for undue experimentation, especially in the light of the tests and dosing information provided herein.

According to the present invention, an obese patient is administered a therapeutically effective amount of active principle. As mentioned above, the dose required can be determined by those skilled in the art without the need for undue experimentation. A "therapeutically effective amount" can be defined as the amount of active principle that is sufficient to cause an adequate loss of weight and to result in the consequent normalisation of metabolic parameters, such as the blood glucose level of the obese patient.

Up to this point a general description has been given of the present invention. With the aid of the following examples, a more detailed description will now be provided, with reference to specific embodiments, aimed at giving a better understanding of the aims, characteristics, advantages and operating methods of the invention. However, the scope of the present invention is not intended to be limited thereby.

Figure 1B:
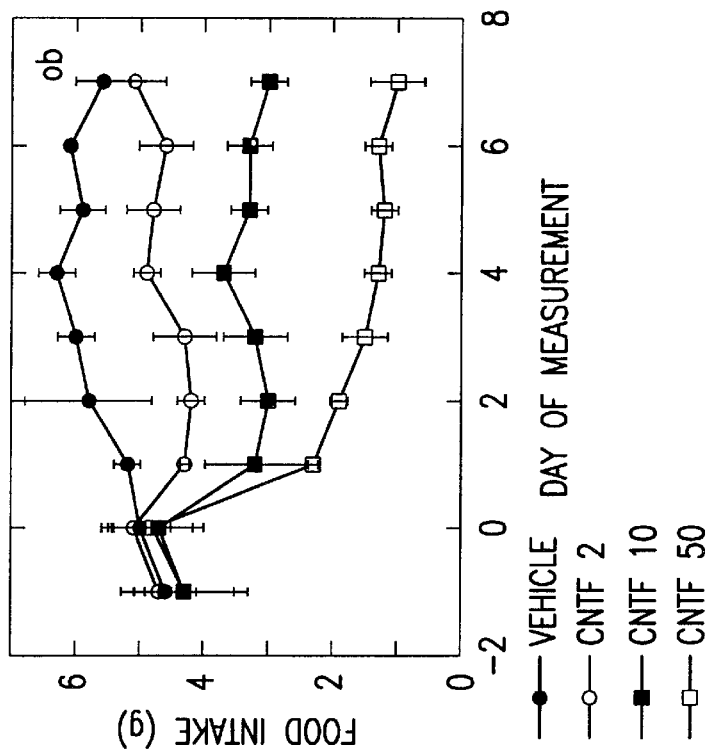
FIG. 1
Figure 1A:
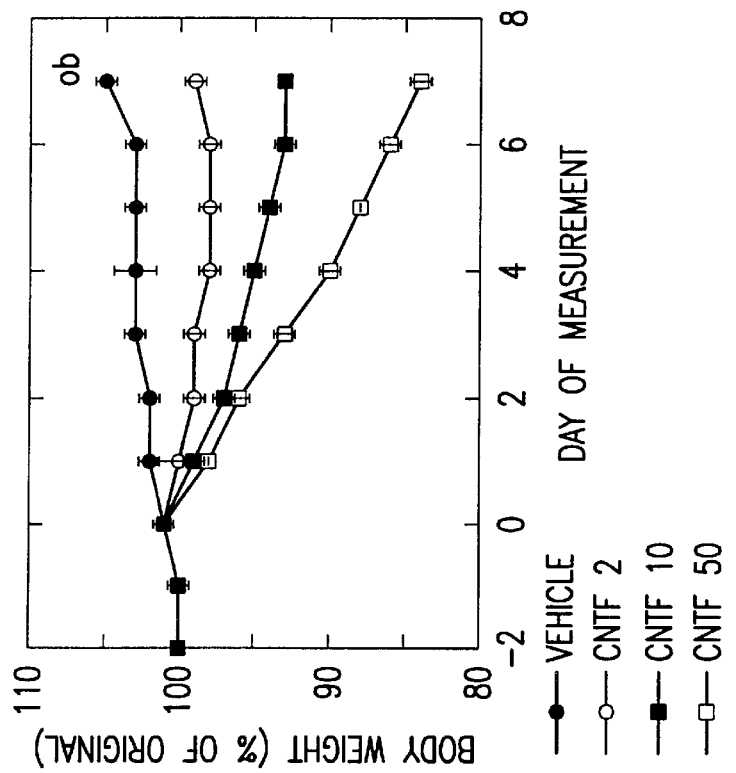
Figure 1D:
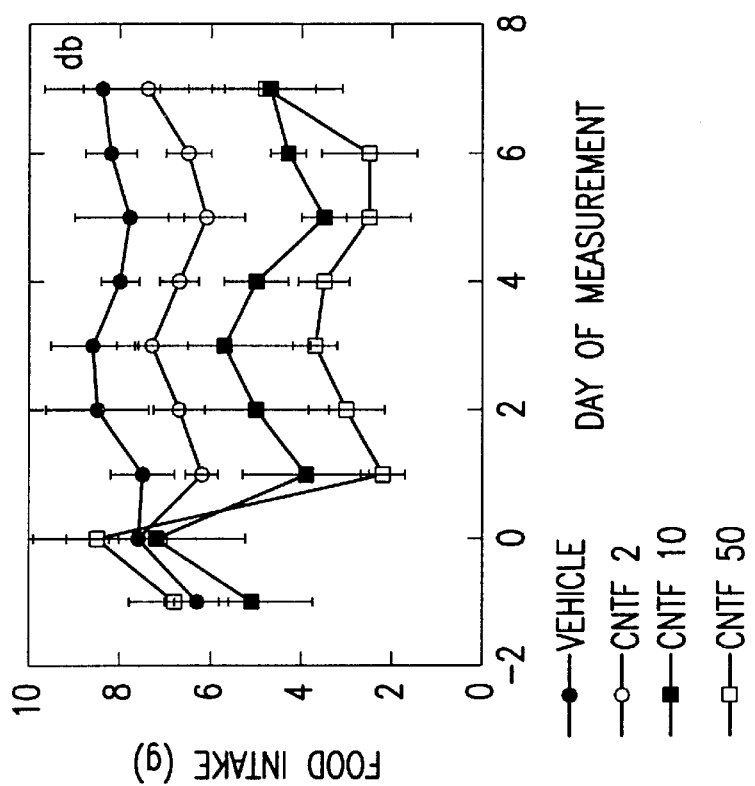
Figure 1C:
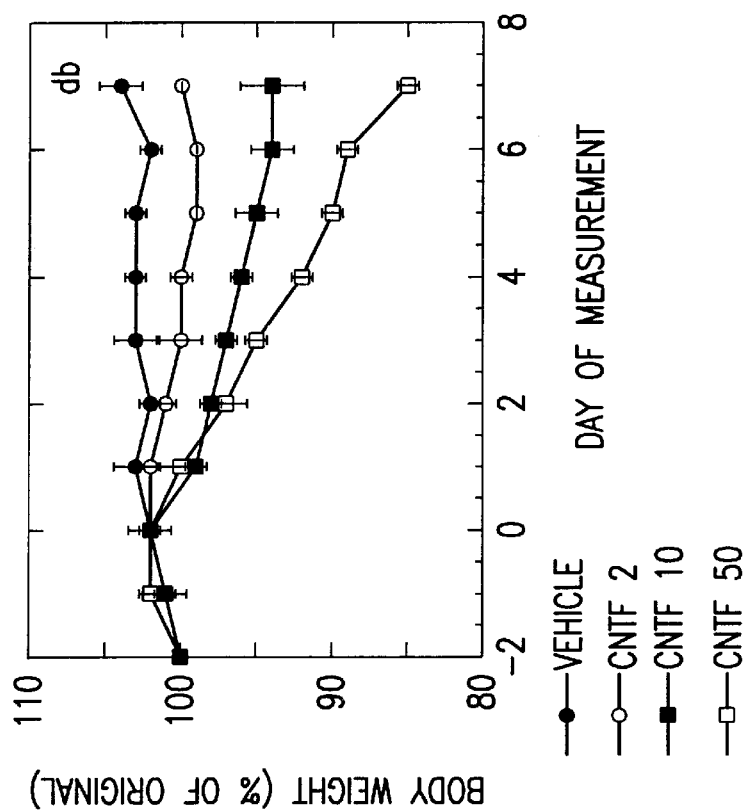
Figure 1E:
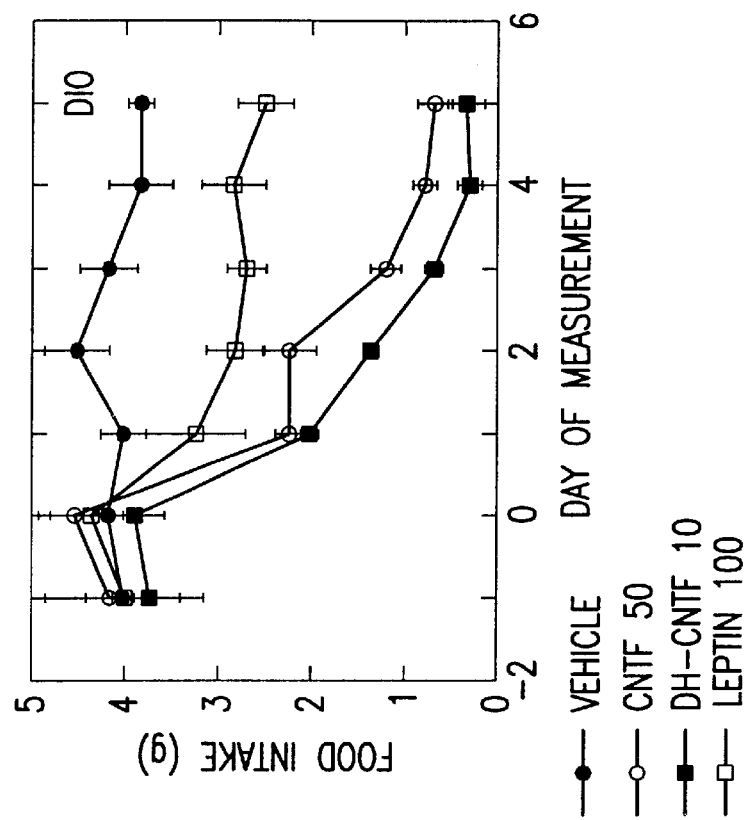
Figure 1F:
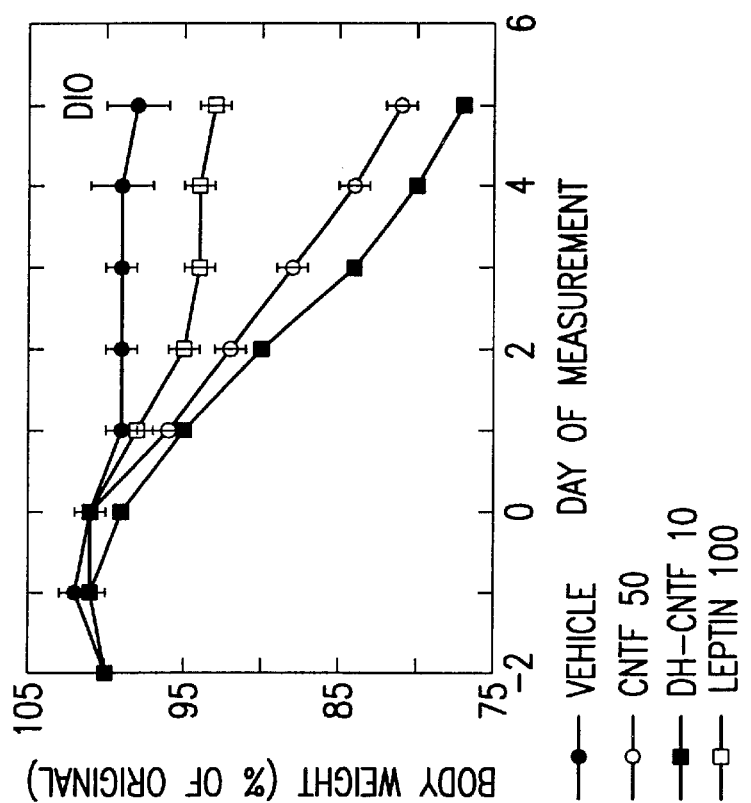

Effects of hCNTF and leptin on body weight (left panels) and food intake (right panels) in genetically obese mice (ob/ob and db/db) and mice with diet-induced obesity (DIO). Mice received daily intraperitoneal injections of either vehicle or proteins (amounts in µg/mouse), starting at day 0. Body weight is expressed as percent of the original weight on day −2 and represents the average±s.e.m (n=3 for ob/ob and db/db, n=5 for DIO mice). Baseline weights for each group of vehicle-treated animals were (in grams): ob/ob, 49.3±0.3; db/db, 39.1±2.5; DIO, 42.6±0.8. Statistical significance was determined by repeated measures ANOVA. For all groups, P-values for the effects of treatment, time, and time x treatment were: $P<0.05$, $P<0.0001$ and $P<0.01$, respectively.

FIG. 2

Effects of hCNTF (2 µ/mouse) and leptin (100 µg/mouse), administered alone or in combination, on weight loss in DIO mice. Mice received daily intraperitoneal injections of the indicated agents.

FIG. 3

Duration of DH-CNTF effects on body weight and food intake in obese vs. lean mice. C57BL/KS db/db mice (circles), or age-and sex-matched C57BL/KS +/+ mice (squares), housed in groups of five, received daily intraperitoneal injections of either vehicle (empty symbols) or 10 µg of DH-CNTF (filled symbols) for 25 days. From day 26, all mice were treated with vehicle. Food intake is the number of grams consumed per group divided by five.

FIG. 4

Effects of DH-CNTF treatment of obese mice on carcass composition. Mice were treated for 10 days by daily intraperitoneal injections of either vehicle or 10 µg of DH-CNTF. Results are the mean ± s.e.m. (n=5). *$P<0.05$; **$P<0.01$ vs. vehicle by Student's t-test.

FIG. 5

Effects of leptin and hCNTF on STAT factor activation in neuronal cell lines. GT-1-7 and SN-56 cells transfected with an expression vector for human OB-Rb were incubated for 10 min in the presence or absence of the indicated cytokines (at 100 ng/ml). Activation of cellular STAT factors was determined by electromobility shift assay. Arrows denote the positions of migration of bound STAT3 homodimers, STAT1:STAT3 heterodimers, and STAT1 homodimers.

FIG. 6

Expression of receptor subunits for leptin (OB-Rb) and CNTF (CNTF receptor-α [CNTFRα] and LIFR) in mouse hypothalamus, as determined by in situ hybridisation. A, arcuate nucleus; P, paraventricular nucleus. (X100)

FIG. 7

Effects of leptin and hCNTF on tis-11 expression in mouse hypothalamus. Groups of three ob/ob mice received intraperitoneal injections of either vehicle, leptin (100 µg) or DH-hCNTF (10 µg) and were sacrificed one hour later by cervical dislocation. In situ hybridization was performed on frozen coronal brain sections from vehicle- or protein-treated mice, using $^{35}$S-labelled cRNA probes specific for murine tis-11. (x 100)

EXAMPLE 1

Anti-obesity Effects of hCNTF and its Mutant DH-CNTF
Methods
Protein Production

Recombinant human CNTF and DH-CNTF were produced in *E. coli* BL21 as previously described (11). The DNA coding sequence for human leptin was assembled by PCR using synthetic oligodeoxyribonucleotides according to the method of Stemmer et al. (12), and subcloned into the bacterial expression plasmid pRSET-5d (13). Human leptin was produced using the same protocol as for hCNTF. All proteins were purified by reverse-phase HPLC (11) in order to remove bacterial lipopolysaccharide. Purified preparations contained less than 5 ng endotoxin/mg protein, as determined by the Limulus amoebocyte assay (Sigma).

Animal Studies

Experiments were performed using groups of male 10–11 week-old C57BL/6J ob/ob and C57BL/KS db/db mice, and 19 week-old AKR/J mice rendered obese by feeding a high-fat diet (14) starting at 12 weeks of age. Except where noted otherwise, animals were housed in individual cages with ad libitum access to water and either standard or high-fat (AKR mice) rodent chow, under a 12 hour light-dark cycle (lights on at 7:30 hr, off at 19:30 hr). They were accustomed to daily (9:00 hr) intraperitoneal injections of vehicle (0.9% saline, 0.2 mg/ml endotoxin-free bovine serum albumin) for two days before the beginning of the treatment (day 0) with either vehicle or cytokines. Animals were weighed after injection and food intake was determined by recording the amount of chow remaining in food dishes.

Results

Human ciliary neurotrophic factor (hCNTF), its mutant DH-CNTF (10) [(Ser166Asp/Gln167His) hCNTF]; a mutant of hCNTF with 40-fold higher affinity for the CNTF a-receptor) and human leptin were tested for biological activity in genetically obese mice, and in mice with diet-induced obesity (DIO). These models of obesity and diabetes are generally accepted in the art as indicative of the obese condition. Agents showing an anti-obesity effect in these models will show a similar effect in other mammals, in particular in man.

As will be seen more clearly in the following, the compounds of the invention are active in all the biological tests mentioned above, and are also found to be anti-obesity agents. Furthermore, they are active in reversing the hyperglycemia and hyperinsulinemia associated with obesity. It is therefore assumed that these compounds will also be of use in the treatment of hyperglycemia in human diabetes mellitus.

In accordance with previous experiments and results (6–8, 15), it was found that systematic administration of leptin to mutant mice, which do not express functional leptin, reverses the obesity and the hyperphagia associated with leptin deficiency. Daily intraperitoneal administration of hCNTF (between 2 and 50 $\mu$g/mouse; corresponding to 40–1000 $\mu$g/kg body weight) to ob/ob mice also produces a progressive and dose-dependent decrease in body weight, as well as a rapid reduction in food intake (FIG. 1). At the highest dose tested (50 $\mu$g; 1000 $\mu$g/kg), hCNTF causes a 16% decrease in body weight after 7 days (compared with a 5% increase in vehicle-treated controls), and a 5-fold decrease in food intake. These effects are comparable in magnitude to those of a 100 $\mu$g (2000 $\mu$g/kg) dose of leptin (13% and 95% reductions in body weight and food intake, respectively; $P<0.0001$ by Student's t-test). The hCNTF variant DH-CNTF produces similar reductions in body weight and food intake at doses approximately 5 times lower than those of hCNTF. This result, together with the lack of activity of hCNTF variants (11) with impaired receptor interaction (data not shown), suggests that the anti-obesity effect of hCNTF is mediated through activation of specific CNTF receptors.

The db/db mutant mouse does not respond to leptin (6–8, 15), because of a mutation in the gene coding for the leptin receptor OB-R, which results in the production of a receptor splice variant with a truncated intracytoplasmic domain (9, 29). In contrast, treatment of db/db mice with hCNTF causes a dose- and time-dependent weight loss and suppression of food intake (FIG. 1). The superagonist DH-CNTF elicited comparable effects at approximately ⅕ the dose of hCNTF. The results obtained in ob/ob and db/db mice show that hCNTF does not act by stimulating the release of leptin or by direct activation of leptin receptors.

AKR mice rendered obese by feeding a high-fat diet (DIO mice) have been previously reported to be less sensitive than ob/ob mice to the weight- and appetite-reducing effects of leptin (7). This finding, together with the observation that plasma levels of leptin are higher in DIO mice than in lean littermates, led to the proposal that diet-induced obesity is associated with leptin resistance (4, 17). As shown in FIG. 1, a 5-day treatment of DIO mice with human leptin (100 $\mu$g; 2500 $\mu$g/kg) causes modest decreases in body weight (7±1%; $p<0.05$ vs. vehicle) and food intake (27±2%; $P<0.05$). In contrast, hCNTF (50 $\mu$g; 1250 $\mu$g/kg) and DH-CNTF (10 $\mu$g; 250 $\mu$g/kg) elicit more extensive reductions in body weight (19±1% and 24±1%, respectively; $P<0.0001$) and food intake (76±4%, and 73±7%, respectively; $P<0.0005$). The discovery that hCNTF can reverse obesity in both db/db and DIO mice has important implications for the treatment of human obesity, which has been postulated to be associated with resistance to leptin (4, 18, 19).

As can be seen, the obese mice received daily intraperitoneal administrations of hCNTF or of the mutant DH-CNTF in doses of from 2 to 50 $\mu$g. corresponding to 50–1000 $\mu$g/kg body weight. At the highest dose, the compounds cause a reduction of over 10% in the body weight after 5 days of treatment. Therefore, doses of hCNTF or DH-CNTF of under 1000 $\mu$g/kg are administered to patients suffering from obesity, preferably doses of approximately 100 $\mu$g/kg, in order to induce a rapid reduction in body weight (5–10%). Furthermore, in this form of preferred embodiment, hCNTF or DH-CNTF is administered once a day and the treatment is continued for a few days, until the required reduction in body weight is obtained.

EXAMPLE 2

Figure 2:
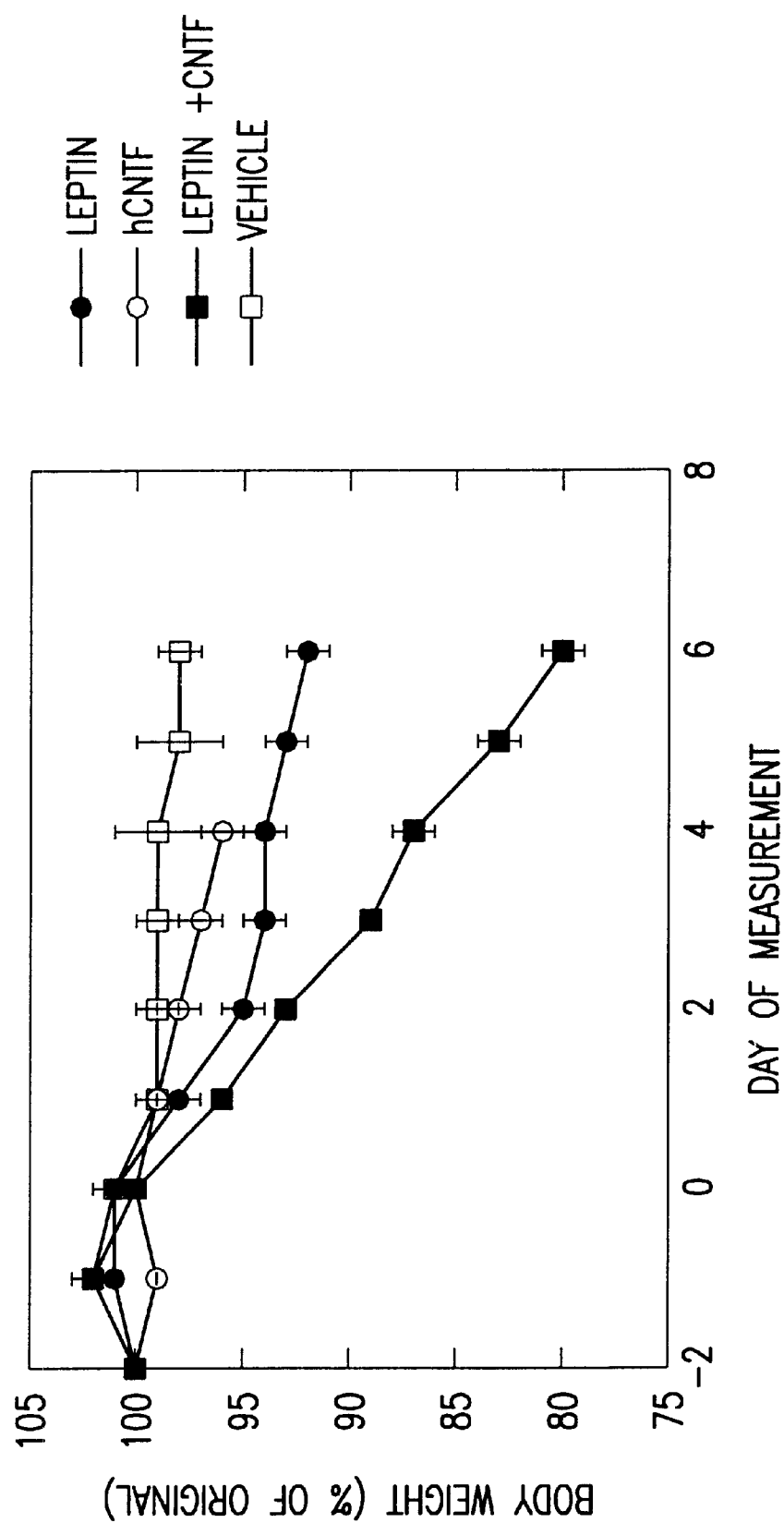

Increase in the Anti-obesity Effect of Leptin Due to Synergism With hCNTF in DIO Mice Obese DIO mice were given daily intraperitoneal injections of leptin (100 $\mu$g; corresponding to 2500 $\mu$g/kg) along with a small dose (2 $\mu$g, corresponding to 50 $\mu$g/kg) of hCNTF. Neither of the two agents produces a significant weight loss per se. This treatment has the effect of producing a strong, synergistic loss of body weight (FIG. 2). This result proves that small doses of hCNTF can be used to give a significant increase in the effect of leptin in a model of obesity associated with a resistance to leptin.

EXAMPLE 3

Duration and Specificity of the Anti-obesity Effects of DH-CNTF

Methods

Behavioral Studies

Locomotor activity was measured by scoring the number of times mice crossed the middle of their home cages during three hours of the dark cycle (21:00 hr–24:00 hr). Grooming behavior was assessed by focal observations in home cages (five observations of 1 min each during 30 min of the light cycle), using a rating scale from 0 to 3 (0, no activity; 1, weak; 2, normal; 3 hyperactive). Conditioned taste aversion was performed using a two-bottle paradigm with 0.1% saccharin as a novel taste (20).

Body Composition

Carcasses were homogenized, and 2-gram aliquots were lyophilized and then oven-dried at 90° until weight was constant. Fat was then extracted with ethyl ether/ethanol (20:1, v/v) (21). Water and fat mass were calculated from the weight differences after dehydration and fat extraction, respectively. Lean mass was defined as the remaining amount of carcass.

Figure 3A:
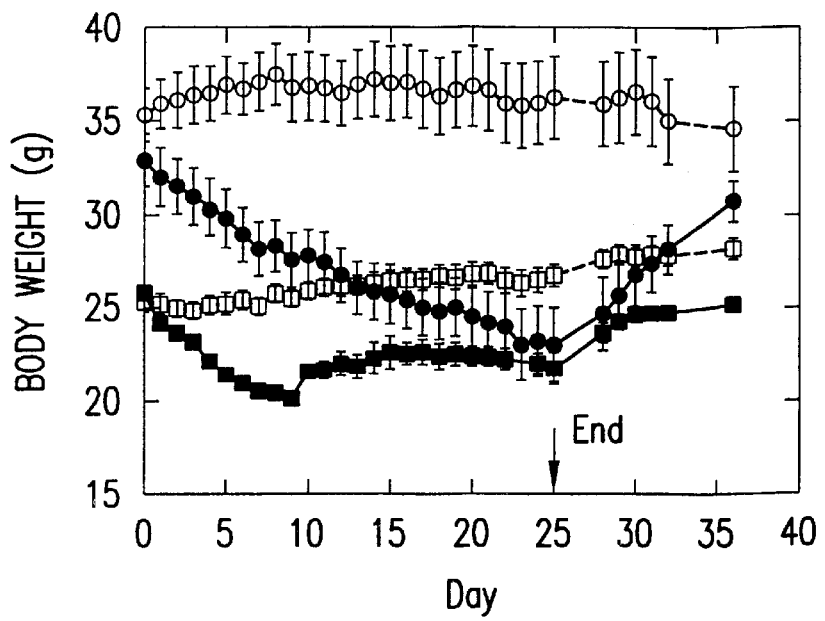
Figure 3B:
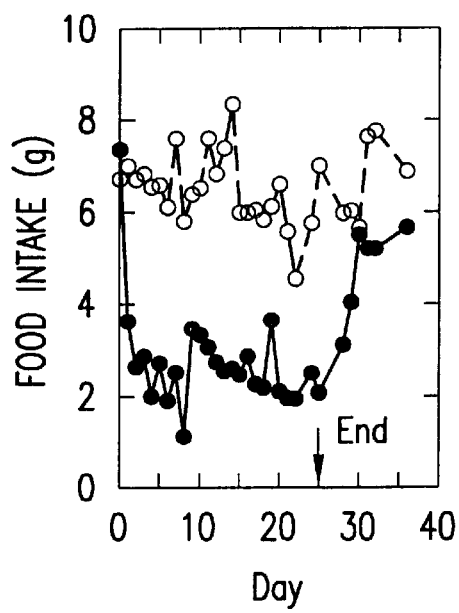
Figure 3C:
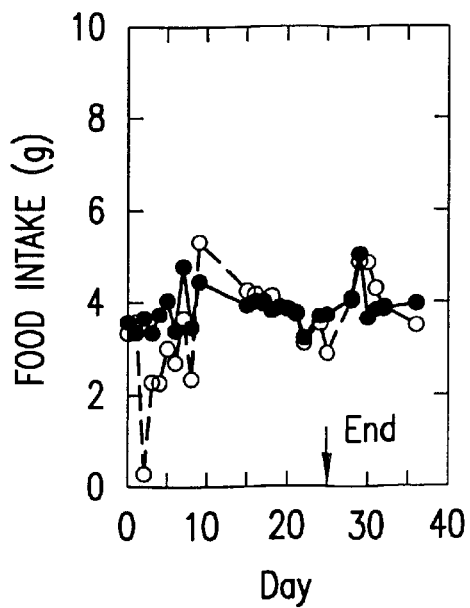

Results hCNTF has previously been reported to cause a transient reduction of body weight and food intake in normal mice (22) Its effects on obese animals have not been studied heretofore. It is therefore important to determine whether or not its effects on obese mice are subject to desensitisation. As shown in FIG. 3, DH-hCNTF produces protracted effects in obese mice. A 25-day treatment of db/db mice with DH-CNTF leads to a progressive and steady decrease in body weight, which by day 8 reaches a level corresponding to that of age- and sex-matched wild-type mice. In parallel, DH-CNTF elicits a ~50% decrease in food intake, which persists throughout the treatment. Similar results were obtained in ob/ob mice treated for 17 days with hCNTF (data not shown). In contrast, DH-CNTF elicits only transient effects in strain-matched wild-type mice. Thus, DH-CNTF rapidly depresses both food intake and the rate of body weight change in lean mice, but these effects subside after approximately 5 and 10 days of treatment, respectively (FIG. 3).

Figures 4A, 4B:
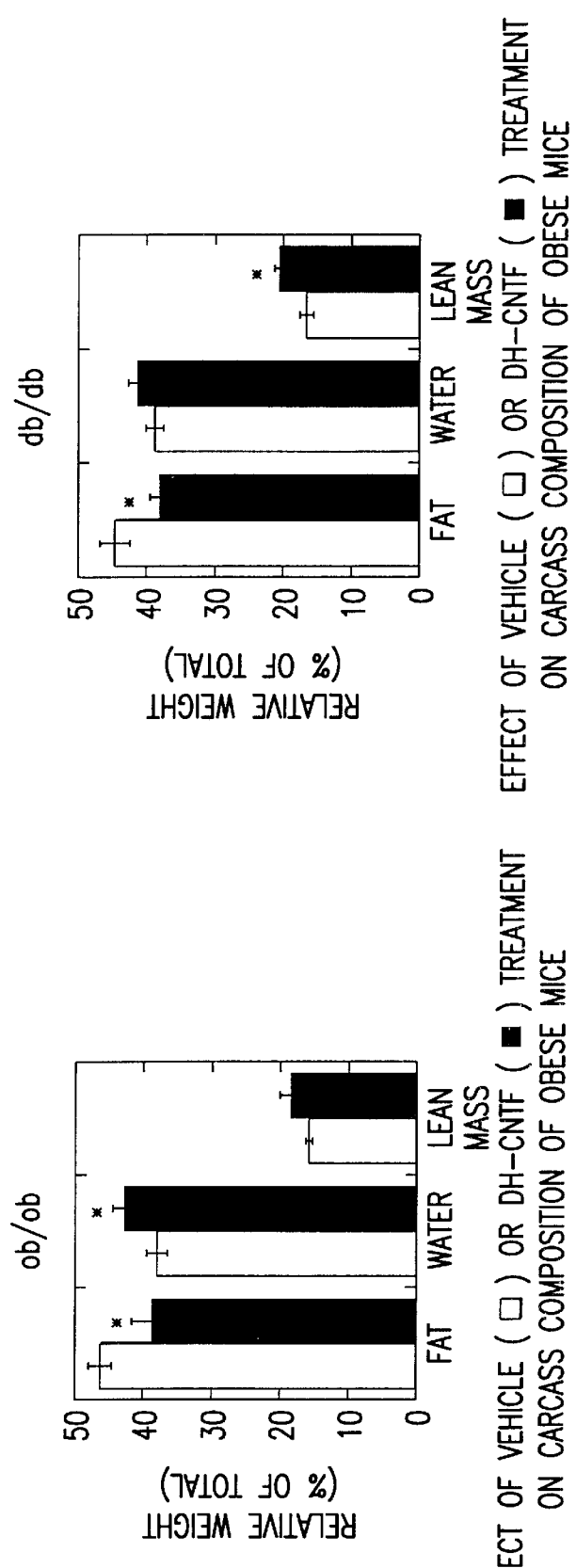
Figures 4C, 4D:
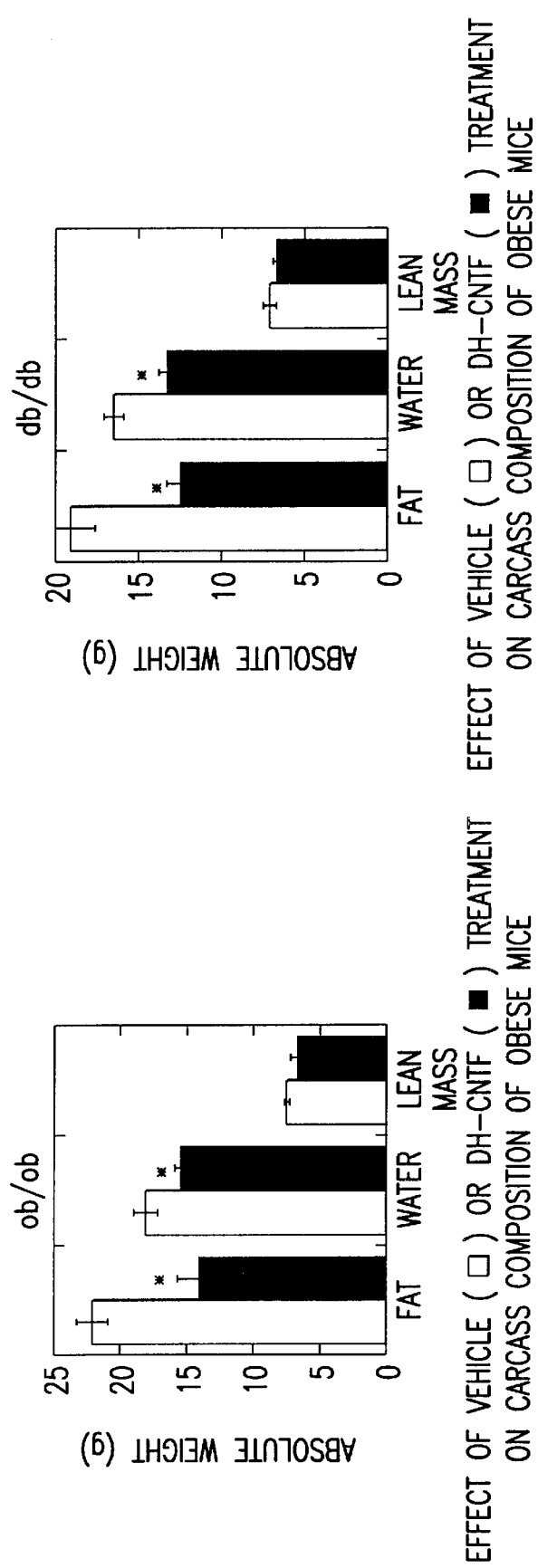

A possible explanation for the observed differences between obese and lean animals is that hCNTF, similarly to leptin (5,6), predominantly depletes adipose tissue mass, such that the extent and duration of its effect would depend on the size of fat depots. Indeed, DH-CNTF specifically reduces the percentage of body fat in ob/ob and db/db mice, while increasing that of body water and lean mass as compared with vehicle-treated controls (FIG. 4). The absolute weight loss induced by DH-CNTF can be accounted for by a predominant loss of body fat (60–70% of lost mass), accompanied by a smaller reduction in water mass (see absolute weights in FIG. 4). Leptin produces similar effects in ob/ob mice (5,6). Thus, in obese mice, hCNTF elicits specific anti-adiposity effects. In contrast, hCNTF has been reported to cause reductions in muscle (23) or protein (24) mass in lean animals. A plausible explanation for this apparent discrepancy is that the predominant fat-depleting effect of hCNTF leads to a nearly total loss of body fat in lean animals (ref. (23) and our unpublished results), which causes protein loss as a secondary event.

hCNTF does not induce toxicity, malaise or illness. Irreversible toxicity was ruled out by the finding that body weight and food intake rapidly return to pretreatment levels following interruption of protein administration, both in db/db (FIGS. 2G, H) and ob/ob mice (data not shown). Locomotor activity is not significantly altered by a 3-day treatment of db/db mice with DH-CNTF (10 µg) as compared to vehicle-treated controls (activity scores: 43±6 and 49±6, respectively; n=5). Likewise, DH-CNTF treatment does not alter grooming behavior (activity scores: 1.2±0.6 and 1.0±0.4, for DH-CNTF and vehicle-treated, respectively). In addition, DH-CNTF does not induce any form of stereotypic behavior. The possibility that the protein causes taste aversion was examined in DIO mice using a two-bottle paradigm with 0.1% saccharin as a novel taste (20). Similarly to leptin, which was reported to reduce water intake in ob/ob mice (5), DH-CNTF (10 µg) causes a decrease in water intake of DIO mice 2 days after conditioning (1.8±0.1 ml vs. 2.8±0.2 ml in vehicle-treated controls; n=9; P<0.001). However, DH-CNTF does not cause taste aversion (saccharin intake 49±2% of total fluid vs. 51±4% in controls). These results indicate that the satiety effect of DH-CNTF is not due to cytokine-induced sickness behavior.

EXAMPLE 4
Reversal of Obesity-associated Metabolic Defects By hCNTF and DH-CNTF Methods Mice received daily intraperitoneal injections of either vehicle, leptin (100 µg), hCNTF (50 pg) or DH-CNTF (10 µg). In pair-feeding experiments (2 and 4), vehicle-treated mice were either fed ad libitum (control) or fed the same amount of chow consumed by DH-CNTF-treated mice during the preceding 24-hour period. Blood samples were taken 24 hours after the last injection (experiments 1 and 3), or 7 hours after the last injection and the removal of food (experiments 2 and 4). Serum glucose was determined by the glucose oxidase method and serum insulin by radioimmunoassay (Amersham), using rat insulin as standard.

Results

In addition to its weight- and appetite-regulating actions, hCNTF and DH-CNTF are able to reverse the hyperglycemia and hyperinsulinemia associated with the ob and db mutations.

Mice bearing the ob mutation on the C57BL/6 background exhibit strong hyperinsulinemia (with nearly normal glucose levels after the age of 2–3 months) (25), which can be corrected by leptin treatment (5,6,15). Treatment of ob/ob mice with hCNTF or DH-CNTF also lead to strong reductions in serum insulin levels (Table 1, experiments 1 and 2). The db/db mutant on the C57BL/KS background is characterized by severe hyperglycemia (with nearly normal insulin levels after the age of 2–3 months) (26). As previously reported (5,6,15), leptin is unable to reverse hyperglycemia in db/db mice. In contrast, hCNTF and DH-hCNTF lead to 2–3-fold reductions in both fed and fasted serum glucose levels, without affecting the already low levels of insulin (Table 1, experiments 3 and 4). The weight-reducing and anti-diabetic effects of DH-CNTF exceed those induced by pair-feeding of ob/ob or db/db mice to the food intake of cytokine-treated animals (Table 1, experiments 2 and 4). These results show that the effects of hCNTF, similarly to those of leptin (6, 27, 28) are not solely due to decreased food intake.

TABLE 1

Effects of leptin, hCNTF and pair-feeding on body weight change and serum insulin and glucose in obese mice

| Treatment | Weight change (g) | Serum glucose (mM) | Serum insulin (ng/ml) |
|---|---|---|---|
| Experiment 1 (ob/ob, 7 days) | | | |
| Vehicle | +1.6 ± 0.1 | nd | 63.3 ± 12.7 |
| Leptin | −6.5 ± 0.4** | nd | 8.1 ± 9.1* |
| hCNTF | −8.2 ± 0.1** | nd | 4.3 ± 1.0* |
| DH-CNTF | −7.7 ± 0.8** | nd | 3.2 ± 2.9* |
| Experiment 2 (ob/ob, 4 days) | | | |
| Vehicle | +0.5 ± 0.5 | nd | 72.5 ± 25.7 |
| DH-CNTF | −8.4 ± 0.5**§ | nd | 8.1 ± 0.2*↑ |
| Pair-fed | −7.0 ± 0.5** | nd | 11.1 ± 0.4* |
| Experiment 3 (db/db, 7 days) | | | |
| Vehicle | +0.2 ± 0.4 | 23.3 ± 0.8 | 9.1 ± 4.2 |
| Leptin | −0.8 ± 0.5 | 28.7 ± 0.8* | 9.7 ± 2.6 |
| hCNTF | −6.8 ± 0.5** | 8.4 ± 1.7** | 8.2 ± 2.1 |
| Experiment 4 (db/db, 4 days) | | | |
| Vehicle | 0.0 ± 0.3 | 30.1 ± 2.0 | nd |
| DH-CNTF | −6.8 ± 0.4**§ | 12.3 ± 1.9**§ | nd |
| Pair-fed | −5.3 ± 0.4** | 24.8 ± 5.4 | nd |

Data are mean values ± s.e.m. from 3–6 animals per treatment group.
nd, not determined.
*P < 0.05 vs. vehicle
**P < 0.001 vs. vehicle
§P < 0.05 vs. pair-fed
↑P < 0.001 vs. pair-fed (Student's t-test).

EXAMPLE 5
hCNTF and Leptin Activate Overlapping neuronal Signaling Systems

Methods

STAT Activation Assay

GT-1-7 and SN-56 cells were maintained in complete culture medium (Dulbecco's modified Eagle medium containing 10% fetal calf serum, penicillin, glutamine and, for SN-56 cells, sodium pyruvate). Cells were plated in 100 mm dishes and used 24 hours later, when semi-confluent. An expression vector containing the entire coding region (nucleotides 141–3770) of human OB-R (29) was prepared as previously described (30) and was transfected into the cells by Lipofectamine (Gibco BRL) according to the manufacturer's instructions. After 24 hours, cells were distributed into 60 mm culture dishes containing complete culture medium, and after an additional 24 hours, they were deprived of serum for 4 hours before a 10 min treatment with different effectors, as specified below. The cells were then washed with ice-cold phosphate-buffered saline containing 50 mM NaF, collected by centrifugation and frozen in liquid nitrogen. Total cell extracts were prepared as previously described (31). Binding of activated STAT factors to the high affinity SIE m67 oligonucleotide (32) was determined by electromobility shift assays according to Sadowsky and Gilman (33), using 10 μg of cell extract. The oligonucleotide probe was labelled by filling in 5' protruding ends with Klenow enzyme in the presence of [a-$^{32}$P]DATP and [a-$^{32}$P] dCTP (3000 Ci/mmol). Complexes were resolved on 5% polyacrylamide/2.5% glycerol/0.5×TBE (45 mM Tris-borate, 0.5 mM EDTA, pH 7.8) gels, which were then dried and subjected to autoradiography.

In Situ Hybridization

Serial coronal brain sections were prepared in the region containing the arcuate and paraventricular hypothalamic nuclei. In situ hybridization was performed according to previously described procedures (34), using $^{35}$S-labelled CRNA probes. Specific probes for murine OB-Rb, CNTFRa, LIFR and tis-11 were obtained by RT-PCR amplification of mouse brain RNA using appropriate oligonucleotide primers, and corresponded to nucleotides 2850–3407, 246–856 (numbering according to the human sequence) 2620–3217, and 1–950 of the respective coding sequences.

Results

Figure 5:
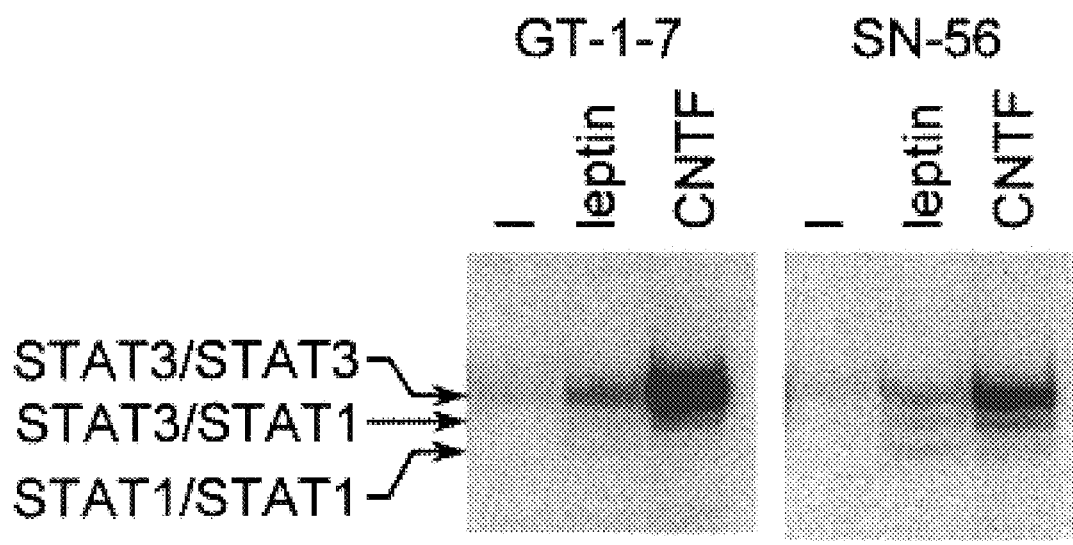

The partially shared biological activities of hCNTF and leptin suggest that these proteins act through similar signaling mechanisms. The ability of hCNTF and leptin to regulate the DNA binding activity of STAT transcription factors was examined in two neuronal cell lines, SN-56 (35) and GT-1-7 (36), derived from mouse septal and hypothalamic neurons, respectively. Cells were transfected with an expression vector for human OB-Rb, the signaling-competent long-form splice variant of OB-R (30, 37, 38). In both neuronal cell lines, hCNTF and leptin trigger the activation of a similar pattern of STAT factors, with predominant DNA binding of STAT3 homodimers and, to a lesser degree, that of STAT1 homodimers and STAT1/STAT3 heterodimers. (FIG. 5). This pattern is characteristic of gp130-signaling cytokines (39), consistent with the sequence similarity, including the presence of consensus motifs for JAK kinase and STAT factor interaction sites, between OB-Rb and receptors of the gp130 family (9).

Figure 6:
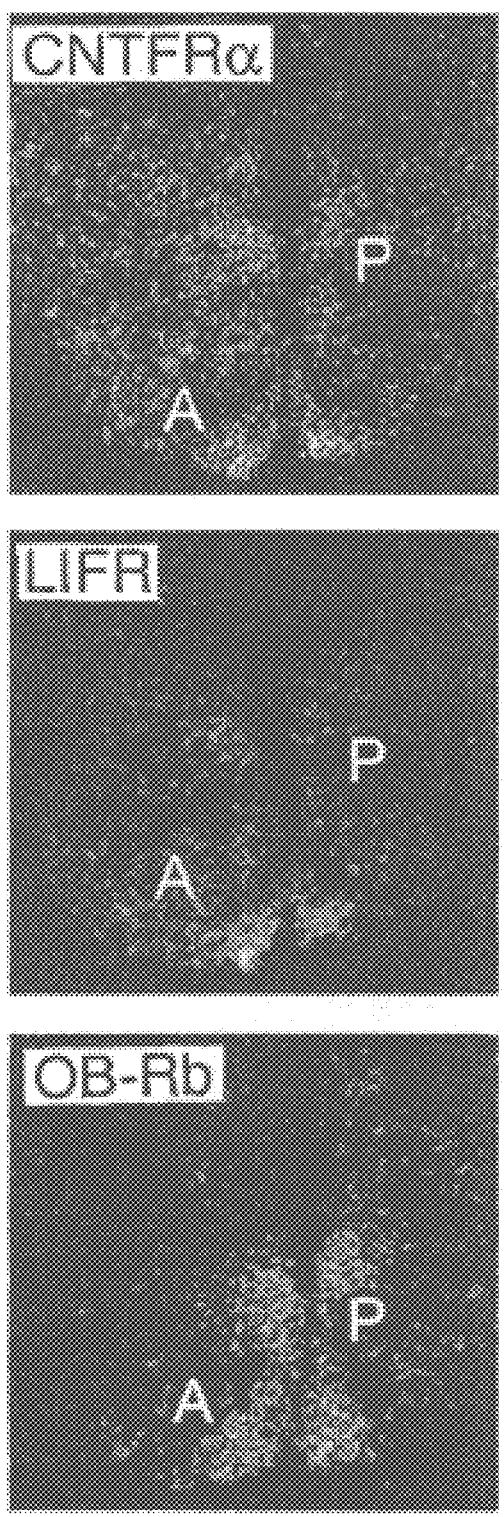

A possible explanation for the overlapping metabolic effects of leptin and hCNTF is that these proteins stimulate common effector pathways in brain areas involved in the regulation of energy intake and expenditure. The long-form OB-Rb splice variant, is predominantly expressed in such regions, including the arcuate, ventromedial and paraventricular hypothalamic nuclei (40,41). To determine whether hypothalamic satiety centers could also be targets for hCNTF, in situ hybridization was performed using cRNA probes specific for murine OB-Rb, CNTFRα and LIFR. As shown in FIG. 6, the arcuate and paraventricular nuclei of the mouse hypothalamus express mRNAs for leptin and CNTF receptor subunits. Preliminary results indicate expression of CNTFRα and LIFR in additional nuclei, including the ventromedial hypothalamus.

Figure 7:
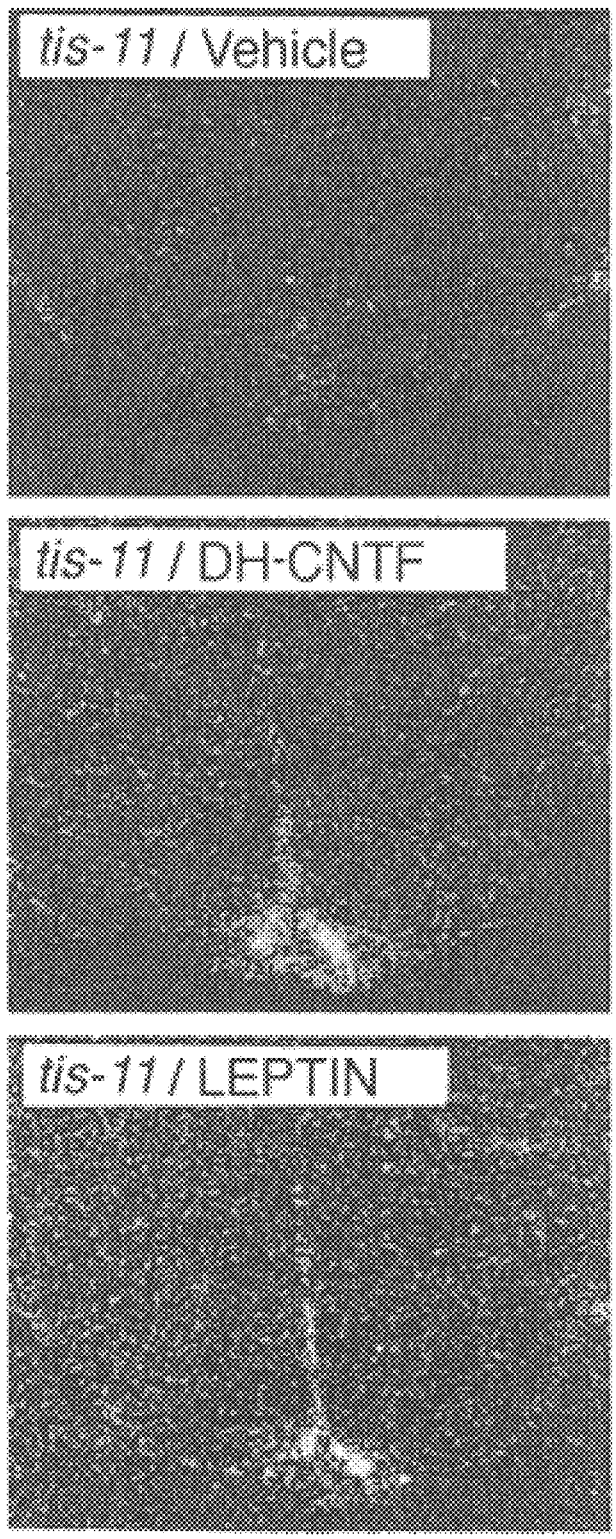

In agreement with the existence of a cytokine signaling pathway to central satiety centers, systemically administered leptin activates early signaling responses in mouse hypothalamus (42, 43). If the mechanism of action of hCNTF is similar to that of leptin, early activation of hypothalamic responses should be detectable also after peripheral administration of hCNTF. The tis-11 primary response gene (44), which is rapidly induced by hCNTF and other Stat3-dependent cytokines (45) was used as a marker for cellular activation. Hypothalamic tis-11 MRNA of ob/ob mice was found to be significantly elevated one hour after intraperitoneal injection of leptin or DH-CNTF as compared to vehicle-treated controls. In situ hybridization revealed that the arcuate nucleus is a major site of tis-11 induction by both cytokines (FIG. 7).

This result demonstrates that systemically administered hCNTF and leptin can induce early signaling responses in a brain region that has been implicated as an important target of leptin action (15, 41). It cannot be excluded that the cytokines activate hypothalamic cells indirectly, for instance through peripheral mediators or via afferent nerves. Yet, the rapidity of this effect, together with the expression of specific receptors for hCNTF and leptin in the arcuate nucleus argue for a direct action consequent to cytokine entry into the hypothalamus. Both hCNTF (46) and leptin (47) can cross the blood-brain barrier. Cytokines may penetrate into the brain via specific transport systems, as reported for leptin (47). They may also gain access to hypothalamic neurons through circumventricular organs lying outside the blood-brain barrier, such as the median eminence, which is adjacent to the arcuate nucleus (48). In conclusion, the present results are consistent with the notion that the partially shared biological activities of hCNTF and leptin involve a related mechanism of action.

EXAMPLE 6
CNTFRα Binding Activities of hCNTF and hCNTF Variants

The relative binding affinities to CNTF receptor-α (CNTFRα) of hCNTF and different hCNTF variants were determined by solid phase binding assay as previously described (10). As shown in Table 2, a number of hCNTF variants possessed greater affinity for CNTFRa than wild-type hCNTF. These variants, like DH-CNTF, have increased utility for treatment of obesity and associated diseases, such as diabetes.

TABLE 2

CNTF receptor α binding of hCNTF and hCNTF variants

| SEQ ID NO: | Name | Abbrevn./ note | Relative Binding (hCNTF = 1) |
|---|---|---|---|
| 1 | hCNTF | wild type | 1.1 ± 0.3 |
| 2 | (Gln167Thr) hCNTF | | 11.8 ± 0.3 |
| 3 | (Lys160Gln/Gln167Thr) hCNTF | | 3.1 ± 1.0 |
| 4 | (Gln167Tyr) hCNTF | | 9.6 ± 2.6 |

TABLE 2-continued

CNTF receptor α binding of hCNTF and hCNTF variants

| SEQ ID NO: | Name | Abbrevn./ note | Relative Binding (hCNTF = 1) |
|---|---|---|---|
| 5 | (Ser166Asp/Gln167His) hCNTF | DH-CNTF | 22.8 ± 3.5 |
| 6 | (Gln163Ser/Gln167His) hCNTF | | 4.1 ± 1.1 |
| 7 | (Gln167Ala) hCNTF | | 9.0 ± 0.7 |
| 8 | (Ser166Ala/Gln167Ala) hCNTF | | 8.1 ± 2.8 |
| 9 | (Ser166Gly/Gln167Ala) hCNTF | | 7.5 ± 2.2 |
| 10 | (Ser166Asn/Gln167Ala) hCNTF | | 12.4 ± 1.2 |
| 11 | (Ser166His/Gln167Ala) hCNTF | | 8.8 ± 2.6 |
| 12 | (Ser166Asp/Gln167Ala) hCNTF | | 13.5 ± 1.7 |
| 13 | (Val161Leu/Gln167Ala) hCNTF | | 8.8 ± 0.4 |
| 14 | (Lys160Gln/Gln167Ala) hCNTF | | 11.7 ± 3.2 |
| 15 | (Gln167Ala/His174Ala) hCNTF | | 3.6 ± 0.8 |
| 16 | (Gln167Ala/Arg177Leu) hCNTF | | 11.7 ± 3.3 |
| 17 | (Gln167Ala/Thr169Ser) hCNTF | | 6.9 ± 1.3 |
| 18 | (Gln167Ala/Thr169Leu) hCNTF | | 9.6 ± 2.2 |
| 19 | (Gln167Ala/Thr169Leu/Phe178Ile) hC | | 8.4 ± 0.4 |
| 20 | (Ser166Asp/Gln167Ala/Thr169Leu) hC | | 21.0 ± 1.6 |
| 21 | (Ser166Asp/Gln167Ala/Arg177Phe) hC | | 13.1 ± 2.0 |
| 22 | (Val170Arg/His174Ala) hCNTF | | 3.3 ± 0.4 |
| 23 | (Phe152Ala/Ser166Asp/Gln167His) hC | | 32 ± 11 |
| 24 | (Lys155Ala/Ser166Asp/Gln167His) hC | | 51 ± 19 |
| 25 | (Gln63Arg) hCNTF | | 2.0 ± 0.3 |
| 26 | (Gln63Arg/Ser166Asp/Gln167His) hCN | | 66 ± 16 |
| 27 | (Asp30Gln/Ser166Asp/Gln167His) hCN | | 30 ± 5 |
| 28 | (Thr169Ile/His174Ala) hCNTP | | 0.07 ± 0.01 |

REFERENCES

1. Weigle, D. S. (1994) *FASEB J.* 8, 302–310
2. Harris, R. B. S. (1990) *FASEB J.* 4, 3310–3318
3. Zhang, Y., Proenca, R., Maffei, M., Barone, M., Leopold, L., and Friedman, J. M. (1994) *Nature* 372, 425–431
4. Maffei, M., Halaas, J., Ravussin, E., Pratley, R. E., Lee, G. H., Zhang, Y., Fei, H., Kim, S., Lallone, R., Ranganathan, S., Kern, P. A., and Friedman, J. M. (1995) *Nature Med.* 1, 1155–1161
5. Pelleymounter, M. A., Cullen, M. J., Baker, M. B., Hecht, R., Winters, D., Boone, T., and Collins, F. (1995) *Science* 269, 540–543
6. Halaas, J. L, Gajiwala, K. S., Maffei, M., Cohen, S. L., Chait, B. T., Rabinowitz, D., Lallone, R. L., Burley, S. K., and Friedman, J. M. (1995) *Science* 269, 543–546
7. Campfield, L. A., Smith, F. J., Guisez, Y., Devos, R., and Burn, P. (1995) *Science* 269, 546–549
8. Bray, G. A. (1996) *Lancet* 348, 140
9. Chen, H., Charlat, O., Tartaglia, L. A., Woolf, E. A., Weng, X., Ellis, S. J., Lakey, N. D., Culpepper, J., Moore, K. J., Breitbart, R. E., Duyk, G. M., Tepper, R. I., and Morgenstern, J. P. (1996) *Cell* 84, 491–495
10. Saggio, I., Gloaguen, I., Poiana, G., and Laufer, R. (1995) *EMBO J.* 14, 3045–3054
11. Di Marco, A., Gloaguen, I., Graziani, R., Paonessa, G., Saggio, I., Hudson, K. R., and Laufer, R. (1996) *Proc. Natl. Acad. Sci. USA* 93, 9247–9252
12. Stemmer, W. P., Crameri, A., Ha, K. D., Brennan, T. M., and Heyneker, H. L. (1995) *Gene* 164, 49–53
13. Schoepfer, R. (1993) *Gene* 124, 83–85
14. West, D. S., Boozer, C. N., Moody, D. L., and Atkinson, R. L. (1992) *Am. J. Physiol.* 262, R1025–R1032
15. Stephens, T. W., Basinski, M., Bristow, P. K., BueValleskey, J. M., Burgett, S. G., Craft, L., Hale, J., Hoffmann, J., Hsiung, H. M., Kriauciunas, A., MacKellar, W., Rosteck, P. R. J., Schoner, B., Smith, D., Tinsley, F. C., Zhang, X.-Y., and Heiman, M. (1995) *Nature* 377, 530–532
16. Lee, G.-H., Proenca, R., Montez, J. M., Carroll, K. M., Darvishzadeh, J. G., Lee, J. I., and Friedman, J. M. (1996) *Nature* 379, 632–635
17. Frederich, R. C., Hamann, A., Anderson, S., Löllmann, B., Lowell, B. B., and Flier, J. S. (1995) *Nature Med.* 1, 1311–1314
18. Hamilton, B. S., Paglia, D., Kwan, A. Y. M., and Deitel, M. (1995) *Nature Med.* 1, 953–956
19. Considine, R. V., Sinha, M. K., Heiman, M. L., Kriauciunas, A., Stephens, T. W., Nyce, M. R., Ohannesian, J. P., Marco, C. C., McKee, L. J., Bauer, T. L., and Caro, J. F. (1996) *N. Engl. J. Med.* 334, 292–295
20. Langhans, W., Harlacher, R., Balkowski, G., and Scharrer, E. (1990) *Physiol. Behav.* 47, 805–813
21. Leshner, A. I., Litwin, V. A., and Squibb, R. L. (1972) *Physiol. Behav.* 9, 281–282
22. Fantuzzi, G., Benigni, F., Sironi, M., Conni, M., Carelli, M., Cantoni, L., Shapiro, L., Dinarello, C. A., Sipe, J. D., and Ghezzi, P. (1995) *Cytokine* 7, 150–156
23. Henderson, J. T., Seniuk, N. A., Richardson, P. M., Gauldie, J., and Roder, J. C. (1994) *J. Clin. Invest.* 93, 2632–2638
24. Espat, N. J., Auffenberg, T., Rosenberg, J. J., Rogy, M., Martin, D., Fang, C. H., Hasselgren, P. O., Copeland, E. M., and Moldawer, L. L. (1996) *Am. J. Physiol.* 271, R185–R190
25. Sprang, S. R. and Bazan, J. F. (1993) *Curr. Opin. Struct. Biol.* 3, 815–827
26. Paonessa, G., Graziani, R., De Serio, A., Savino, R., Ciapponi, L., Lahm, A., Salvati, A. L., Toniatti, C., and Ciliberto, G. (1995) *EMBO J.* 14, 1942–1951
27. Levin, N., Nelson, C., Gurney, A., Vandlen, R., and De Sauvage, F. (1996) *Proc. Natl. Acad. Sci. USA* 93, 1726–1730
28. Schwartz, M. W., Baskin, D. G., Bukowski, T. R., Kuijper, J. L., Foster, D., Lasser, G., Prunkard, D. E., Porte, D. Jr., Woods, S. C., Seeley, R. J., and Weigle, D. S. (1996) *Diabetes* 45, 531–535
29. Tartaglia, L. A., Dembski, M., Weng, X., Deng, N., Culpepper, J., Devos, R., Richards, G. J., Campfield, L. A., Clark, F. T., Deeds, J., Muir, C., Sanker, S., Moriarty, A., Moore, K. J., Smutko, J. S., Mays, G. G., Woolf, E. A., Monroe, C. A., and Tepper, R. I. (1995) *Cell* 83, 1263–1271
30. Rosenblum, C. I., Tota, M., Cully, D., Smith, T., Collum, R., Qureshi, S., Hess, J. F., Phillips, M. S., Hey, P. J., Vongs, A., Fong, T. M., Xu, L., Chen, H. Y., Smith, R. G., Schindler, C., and Van der Ploeg, L. H. T. (1996) *Endocrinology* 137, 5178–5181
31. Demartis, A., Bernassola, F., Savino, R., Melino, G., and Ciliberto, G. (1996) *Cancer Res.* 56, 4213–4218
32. Wagner, B. J., Hayes, T. E., Hoban, C. J., and Cochran, B. H. (1990) *EMBO J.* 9, 4477–4484
33. Sadowski, H. B. and Gilman, M. Z. (1993) *Nature* 362, 79–83
34. Lazzaro, D., Price, M., De Felice, M., and Di Lauro, R. (1991) *Development* 113, 1093–1104
35. Lee, H. J., Hammond, D. N., Large, T. H.,.and Wainer, B. H. (1990) *Dev. Brain Res.* 52, 219–228
36. Mellon, P. L., Windle, J. J., Goldsmith, P. C., Padula, C. A., Roberts, J. L., and Weiner, R. I. (1990) *Neuron* 5, 1–10
37. Ghilardi, N., Ziegler, S., Wiestner, A., Stoffel, R., Heim, M. H., and Skoda, R. C. (1996) *Proc. Natl. Acad. Sci. USA* 93, 6231–6235
38. Baumann, H., Morella, K. K., White, D. W., Dembski, M., Bailon, P. S., Kim, H., Lai, C.-F., and Tartaglia, L. A. (1996) *Proc. Natl. Acad. Sci. USA* 93, 8374–8378

39. Schindler, C. and Darnell, J. E. (1995) *Annu. Rev. Biochem.* 64, 621–651
40. Mercer, J. G., Hoggard, N., Williams, L. M., Lawrence, C. B., Hannah, L. T., and Trayhurn, P. (1996) *FEBS Lett.* 387, 113–116
41. Schwartz, M. W., Seeley, R. J., Campfield, L. A., Burn, P., and Baskin, D. G. (1996) *J. Clin. Invest.* 98, 1101–1106
42. Woods, A. J. and Stock, M. J. (1996) *Nature* 381, 745–740
43. Vaisse, C., Halaas, J. L, Horvath, C. M., Darnell, J. E. Jr., Stoffel, M., and Friedman, J. M. (1996) *Nature Gen.* 14, 95–97
44. Varnum, B. C., Ma, Q., Chi, T., Fletcher, B., and Herschman, H. R. (1991) *Mol. Cell. Biol.* 11, 1754–1758
45. Ip, N. Y., McClain, J., Barrezueta, N. X., Aldrich, T. H., Pan, L., Li, Y., Wiegand, S. J., Friedman, B., Davis, S., and Yancopoulos, G. D. (1993) *Neuron* 10, 89–102
46. Poduslo, J. F. and Curran, G. L. (1996) *Mol. Brain Res.* 36, 280–286
47. Banks, W. A., Kastin, A. J., and Gutierrez, E. G (1994) *Neurosci. Lett.* 179, 53–56
48. Johnson, A. K. and Gross, P. M. (1993) *FASEB J.* 7, 678–686

What is claimed is:

1. A method of treating obesity and diseases associated therewith in a patient comprising the step of administering to said patient an effective amount of a substance that activates the CNTF (ciliary neurotrophic factor) receptor.

2. The method of claim 1, wherein said substance that activates the CNTF receptor is hCNTF (human ciliary neurotrophic factor) or a mutant thereof.

3. The method of claim 2, wherein said substance that activates the CNTF receptor is either a polypeptide consisting of the sequence of SEQ ID NOs: 23, 24, 25, 26, 27, 28 or a modified version of SEQ ID NO: 1, wherein said modified version of SEQ. ID. NO. 1 has amino acid positions 159 to 178 replaced with a sequence selected from the group consisting of SEQ ID NO: 2 to SEQ ID NO: 22.

4. The method of claim 3, wherein said substance that activates the CNTF receptor is said modified version of SEQ ID NO: 1 wherein amino acids 159 to 178 are replaced with SEQ ID NO:5.

5. A method of treating obesity and diseases associated therewith in a patient comprising the step of providing to said patient an effective amount of DNA coding for hCNTF or mutants thereof.

6. The method of claim 5, wherein said DNA codes for either a polypeptide consisting of the sequence of SEQ ID NOs: 23, 24, 25, 26, 27, 28 or a modified version of SEQ ID NO: 1, wherein said modified version of SEQ ID NO: 1 has amino acid positions 159 to 178 replaced with a sequence selected from the group consisting of SEQ ID NO: 2 to SEQ ID NO: 22.

7. The method of claim 5, wherein said DNA codes for a modified version of SEQ ID NO: 1 wherein amino acids 159 to 178 are replaced with SEQ ID NO: 5.

8. A method of treating a human obese patient comprising the step of administering to said patient an effective amount of a CNTF (ciliary neurotrophic factor) receptor activating substance to cause a weight reduction in said patient.

9. The method of claim 8, wherein said substance is hCNTF (human ciliary neurotrophic factor) or a mutant thereof.

10. The method of claim 9, wherein said substance is either a polypeptide consisting of the sequence of SEQ ID NOs: 23, 24, 25, 26, 27, 28 or a modified version of SEQ ID NO: 1, wherein said modified version of SEQ ID NO: 1 has amino acid positions 159 to 178 replaced with a sequence selected from the group consisting of SEQ ID NO: 2 to SEQ ID NO: 22.

11. The method of claim 10, wherein said substance is said modified version of SEQ ID NO: 1 wherein amino acids 159 to 178 are replaced with SEQ ID NO: 5.

12. The method of claim 8, further comprising the use of leptin in an amount sufficient to synergistically enhance weight reduction.

13. The method of claim 12, wherein said substance is hCNTF (human ciliary neurotrophic factor) or a mutant thereof.

14. The method of claim 13, wherein the ratio of said hCNTF or said mutant thereof to leptin is 1:500 to 1:5.

15. The method of claim 14, wherein said ratio is 1:100 to 1:25.

16. The method of claim 8, wherein said weight reduction is primarily due to a loss of body fat.

17. The method of claim 9, wherein said weight reduction is primarily due to a loss of body fat.

18. The method of claim 10, wherein said weight reduction is primarily due to a loss of body fat.

19. The method of claim 8, wherein said patient has diabetes mellitus.

20. The method of claim 9, wherein said patient has diabetes mellitus.

21. The method of claim 10, wherein said patient has diabetes mellitus.

22. The method of claim 16, wherein said patient has diabetes mellitus.

* * * * *

UNITED STATES PATENT AND TRADEMARK OFFICE
CERTIFICATE OF CORRECTION

PATENT NO. : 6,565,869 B1
APPLICATION NO. : 09/308368
DATED : May 20, 2003
INVENTOR(S) : Gennaro Ciliberto et al.

It is certified that error appears in the above-identified patent and that said Letters Patent is hereby corrected as shown below:

On the Title page, item [75], the inventorship should be changed to the following:

Gennaro Ciliberto, Rome (IT)
Isabelle Gloaguen, Scoppito L'Aquile (IT)
Annalise Di Marco, Rieti (IT)
Anna De Martis, Rome (IT)
Ralph Laufer, Rome (IT)
Riccardo Cortese, Rome (IT)

Signed and Sealed this

Thirty-first Day of July, 2007

JON W. DUDAS
*Director of the United States Patent and Trademark Office*

SEQUENCE LISTING

<160> NUMBER OF SEQ ID NOS: 28

<210> SEQ ID NO 1
<211> LENGTH: 200
<212> TYPE: PRT
<213> ORGANISM: Human

<400> SEQUENCE: 1

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```

<210> SEQ ID NO 2
<211> LENGTH: 20
<212> TYPE: PRT
<213> ORGANISM: Artificial Sequence
<220> FEATURE:
<223> OTHER INFORMATION: (Gln167Thr) hCNTF sequence from position 159 to position 178

<400> SEQUENCE: 2

Leu Lys Val Leu Gln Glu Leu Ser Thr Trp Thr Val Arg Ser Ile His

```
                 1               5                   10                  15
Asp Leu Arg Phe
                20

<210> SEQ ID NO 3
<211> LENGTH: 20
<212> TYPE: PRT
<213> ORGANISM: Artificial Sequence
<220> FEATURE:
<223> OTHER INFORMATION: (Lys160Gln/Gln167Thr) hCNTF sequence from
      position 159 to position 178

<400> SEQUENCE: 3

Leu Gln Val Leu Gln Glu Leu Ser Thr Trp Thr Val Arg Ser Ile His
 1               5                   10                  15

Asp Leu Arg Phe
                20

<210> SEQ ID NO 4
<211> LENGTH: 20
<212> TYPE: PRT
<213> ORGANISM: Artificial Sequence
<220> FEATURE:
<223> OTHER INFORMATION: (Gln167Tyr) hCNTF sequence from position 159 to
      position 178

<400> SEQUENCE: 4

Leu Lys Val Leu Gln Glu Leu Ser Tyr Trp Thr Val Arg Ser Ile His
 1               5                   10                  15

Asp Leu Arg Phe
                20

<210> SEQ ID NO 5
<211> LENGTH: 20
<212> TYPE: PRT
<213> ORGANISM: Artificial Sequence
<220> FEATURE:
<223> OTHER INFORMATION: (Ser166Asp/Gln167His) hCNTF sequence from
      position 159 to position 178

<400> SEQUENCE: 5

Leu Lys Val Leu Gln Glu Leu Asp His Trp Thr Val Arg Ser Ile His
 1               5                   10                  15

Asp Leu Arg Phe
                20

<210> SEQ ID NO 6
<211> LENGTH: 20
<212> TYPE: PRT
<213> ORGANISM: Artificial Sequence
<220> FEATURE:
<223> OTHER INFORMATION: (Gln163Ser/Gln167His) hCNTF sequence from
      position 159 to position 178

<400> SEQUENCE: 6

Leu Lys Val Leu Ser Glu Leu Ser His Trp Thr Val Arg Ser Ile His
 1               5                   10                  15

Asp Leu Arg Phe
                20

<210> SEQ ID NO 7
<211> LENGTH: 20
<212> TYPE: PRT
<213> ORGANISM: Artificial Sequence
<220> FEATURE:
```

<223> OTHER INFORMATION: (Gln167Ala) hCNTF sequence from position 159
      to position 178

<400> SEQUENCE: 7

Leu Lys Val Leu Gln Glu Leu Ser Ala Trp Thr Val Arg Ser Ile His
1               5                   10                  15

Asp Leu Arg Phe
            20

<210> SEQ ID NO 8
<211> LENGTH: 20
<212> TYPE: PRT
<213> ORGANISM: Artificial Sequence
<220> FEATURE:
<223> OTHER INFORMATION: (Ser166Ala/Gln167Ala) hCNTF sequence from
      position 159 to position 178

<400> SEQUENCE: 8

Leu Lys Val Leu Gln Glu Leu Ala Ala Trp Thr Val Arg Ser Ile His
1               5                   10                  15

Asp Leu Arg Phe
            20

<210> SEQ ID NO 9
<211> LENGTH: 20
<212> TYPE: PRT
<213> ORGANISM: Artificial Sequence
<220> FEATURE:
<223> OTHER INFORMATION: (Ser166Gly/Gln167Ala) hCNTF sequence from
      position 159 to position 178

<400> SEQUENCE: 9

Leu Lys Val Leu Gln Glu Leu Gly Ala Trp Thr Val Arg Ser Ile His
1               5                   10                  15

Asp Leu Arg Phe
            20

<210> SEQ ID NO 10
<211> LENGTH: 20
<212> TYPE: PRT
<213> ORGANISM: Artificial Sequence
<220> FEATURE:
<223> OTHER INFORMATION: (Ser166Asn/Gln167Ala) hCNTF sequence from
      position 159 to position 178

<400> SEQUENCE: 10

Leu Lys Val Leu Gln Glu Leu Asn Ala Trp Thr Val Arg Ser Ile His
1               5                   10                  15

Asp Leu Arg Phe
            20

<210> SEQ ID NO 11
<211> LENGTH: 20
<212> TYPE: PRT
<213> ORGANISM: Artificial Sequence
<220> FEATURE:
<223> OTHER INFORMATION: (Ser166His/Gln167Ala) hCNTF sequence from
      position 159 to position 178

<400> SEQUENCE: 11

Leu Lys Val Leu Gln Glu Leu His Ala Trp Thr Val Arg Ser Ile His
1               5                   10                  15

Asp Leu Arg Phe
            20

```
<210> SEQ ID NO 12
<211> LENGTH: 20
<212> TYPE: PRT
<213> ORGANISM: Artificial Sequence
<220> FEATURE:
<223> OTHER INFORMATION: (Ser166Asp/Gln167Ala) hCNTF sequence from
      position 159 to position 178

<400> SEQUENCE: 12

Leu Lys Val Leu Gln Glu Leu Asp Ala Trp Thr Val Arg Ser Ile His
 1               5                  10                  15

Asp Leu Arg Phe
            20

<210> SEQ ID NO 13
<211> LENGTH: 20
<212> TYPE: PRT
<213> ORGANISM: Artificial Sequence
<220> FEATURE:
<223> OTHER INFORMATION: (Val161Leu/Gln167Ala) hCNTF sequence from
      position 159 to position 178

<400> SEQUENCE: 13

Leu Lys Leu Leu Gln Glu Leu Ser Ala Trp Thr Val Arg Ser Ile His
 1               5                  10                  15

Asp Leu Arg Phe
            20

<210> SEQ ID NO 14
<211> LENGTH: 20
<212> TYPE: PRT
<213> ORGANISM: Artificial Sequence
<220> FEATURE:
<223> OTHER INFORMATION: (Lys160Gln/Gln167Ala) hCNTF sequence from
      position 159 to position 178

<400> SEQUENCE: 14

Leu Gln Val Leu Gln Glu Leu Ser Ala Trp Thr Val Arg Ser Ile His
 1               5                  10                  15

Asp Leu Arg Phe
            20

<210> SEQ ID NO 15
<211> LENGTH: 20
<212> TYPE: PRT
<213> ORGANISM: Artificial Sequence
<220> FEATURE:
<223> OTHER INFORMATION: (Gln167Ala/His174Ala) hCNTF sequence from
      position 159 to position 178

<400> SEQUENCE: 15

Leu Lys Val Leu Gln Glu Leu Ser Ala Trp Thr Val Arg Ser Ile Ala
 1               5                  10                  15

Asp Leu Arg Phe
            20

<210> SEQ ID NO 16
<211> LENGTH: 20
<212> TYPE: PRT
<213> ORGANISM: Artificial Sequence
<220> FEATURE:
<223> OTHER INFORMATION: (Gln167Ala/Arg177Leu) hCNTF sequence from
      position 159 to position 178

<400> SEQUENCE: 16
```

Leu Lys Val Leu Gln Glu Leu Ser Ala Trp Thr Val Arg Ser Ile His
 1               5                   10                  15

Asp Leu Leu Phe
            20

<210> SEQ ID NO 17
<211> LENGTH: 20
<212> TYPE: PRT
<213> ORGANISM: Artificial Sequence
<220> FEATURE:
<223> OTHER INFORMATION: (Gln167Ala/Thr169Ser) hCNTF sequence from
      position 159 to position 178

<400> SEQUENCE: 17

Leu Lys Val Leu Gln Glu Leu Ser Ala Trp Ser Val Arg Ser Ile His
 1               5                   10                  15

Asp Leu Arg Phe
            20

<210> SEQ ID NO 18
<211> LENGTH: 20
<212> TYPE: PRT
<213> ORGANISM: Artificial Sequence
<220> FEATURE:
<223> OTHER INFORMATION: (Gln167Ala/Thr169Leu) hCNTF sequence from
      position 159 to position 178

<400> SEQUENCE: 18

Leu Lys Val Leu Gln Glu Leu Ser Ala Trp Leu Val Arg Ser Ile His
 1               5                   10                  15

Asp Leu Arg Phe
            20

<210> SEQ ID NO 19
<211> LENGTH: 20
<212> TYPE: PRT
<213> ORGANISM: Artificial Sequence
<220> FEATURE:
<223> OTHER INFORMATION: (Gln167Ala/Thr169Leu/Phe178Ile) hCNTF sequence
      from position 159 to position 178

<400> SEQUENCE: 19

Leu Lys Val Leu Gln Glu Leu Ser Ala Trp Leu Val Arg Ser Ile His
 1               5                   10                  15

Asp Leu Arg Ile
            20

<210> SEQ ID NO 20
<211> LENGTH: 20
<212> TYPE: PRT
<213> ORGANISM: Artificial Sequence
<220> FEATURE:
<223> OTHER INFORMATION: (Ser166Asp/Gln167Ala/Thr169Leu) hCNTF sequence
      from position 159 to position 178

<400> SEQUENCE: 20

Leu Lys Val Leu Gln Glu Leu Asp Ala Trp Leu Val Arg Ser Ile His
 1               5                   10                  15

Asp Leu Arg Phe
            20

<210> SEQ ID NO 21
<211> LENGTH: 20
<212> TYPE: PRT
<213> ORGANISM: Artificial Sequence

```
<220> FEATURE:
<223> OTHER INFORMATION: (Ser166Asp/Gln167Ala/Arg177Phe) hCNTF sequence
      from position 159 to position 178

<400> SEQUENCE: 21

Leu Lys Val Leu Gln Glu Leu Asp Ala Trp Thr Val Arg Ser Ile His
 1               5                  10                  15
Asp Leu Phe Phe
            20

<210> SEQ ID NO 22
<211> LENGTH: 20
<212> TYPE: PRT
<213> ORGANISM: Artificial Sequence
<220> FEATURE:
<223> OTHER INFORMATION: (Val170Arg/His174Ala) hCNTF sequence from
      position 159 to position 178

<400> SEQUENCE: 22

Leu Lys Val Leu Gln Glu Leu Ser Gln Trp Thr Arg Arg Ser Ile Ala
 1               5                  10                  15
Asp Leu Arg Phe
            20

<210> SEQ ID NO 23
<211> LENGTH: 200
<212> TYPE: PRT
<213> ORGANISM: Artificial Sequence
<220> FEATURE:
<223> OTHER INFORMATION: (Phe152Ala/Ser166Asp/Gln167His) hCNTF sequence
      from position 1 to position 200

<400> SEQUENCE: 23

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
130                 135                 140

Asn Val Gly Asp Gly Gly Leu Phe Glu Lys Lys Leu Trp Gly Leu Gln
145                 150                 155                 160

Val Leu Gln Glu Leu Asp His Trp Thr Val Arg Ser Ile His Asp Leu
                165                 170                 175

Arg Phe Ile Ser Ser His Thr Thr Gly Ile Pro Ala Arg Gly Ser His
            180                 185                 190

Tyr Ile Ala Asn Asn Lys Lys Met
            195                 200
```

<210> SEQ ID NO 24
<211> LENGTH: 200
<212> TYPE: PRT
<213> ORGANISM: Artificial Sequence
<220> FEATURE:
<223> OTHER INFORMATION: (Lys155Ala/Ser166Asp/Gln167His) hCNTF sequence
      from position 1 to position 200

<400> SEQUENCE: 24

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
130                 135                 140

Asn Val Gly Asp Gly Gly Leu Phe Glu Lys Ala Leu Trp Gly Leu Lys
145                 150                 155                 160

Val Leu Gln Glu Leu Asp His Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 25
<211> LENGTH: 200
<212> TYPE: PRT
<213> ORGANISM: Artificial Sequence
<220> FEATURE:
<223> OTHER INFORMATION: (Q63R) hCNTF sequence from position 1 to
      position 200

<400> SEQUENCE: 25

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Arg Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

```
His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
    115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 26
<211> LENGTH: 200
<212> TYPE: PRT
<213> ORGANISM: Artificial Sequence
<220> FEATURE:
<223> OTHER INFORMATION: (Gln63Arg/Ser166Asp/Gln167His) hCNTF sequence
      from positioin 1 to position 200

<400> SEQUENCE: 26

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Arg Trp
50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
    115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Asp His Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 27
<211> LENGTH: 200
<212> TYPE: PRT
<213> ORGANISM: Artificial Sequence
<220> FEATURE:
<223> OTHER INFORMATION: (Asp30Gln/Ser166Asp/Gln167His) hCNTF sequence
      from position 1 to position 200
```

```
<400> SEQUENCE: 27

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Gln Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
     50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Asp His Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 28
<211> LENGTH: 200
<212> TYPE: PRT
<213> ORGANISM: Artificial Sequence
<220> FEATURE:
<223> OTHER INFORMATION: (Thr169Ile/His174Ala) hCNTF sequence from
      position 1 to position 200

<400> SEQUENCE: 28

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
     50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140
```

-continued

```
Asn Val Gly Asp Gly Leu Phe Glu Lys Leu Trp Gly Leu Lys
145             150             155             160

Val Leu Gln Glu Leu Ser Gln Trp Ile Val Arg Ser Ile Ala Asp Leu
            165             170             175

Arg Phe Ile Ser Ser His Gln Thr Gly Ile Pro Ala Arg Gly Ser His
            180             185             190

Tyr Ile Ala Asn Asn Lys Lys Met
            195             200
```